(12) United States Patent
Kasic, II et al.

(10) Patent No.: US 7,326,171 B2
(45) Date of Patent: Feb. 5, 2008

(54) ADJUSTABLE BONE BRACKET

(75) Inventors: James Frank Kasic, II, Boulder, CO (US); William J. Simms, Louisville, CO (US); Dana Daniel Tompkins, Frederick, CO (US)

(73) Assignee: Otologics, LLC, Boulder, CO (US)

( * ) Notice: Subject to any disclaimer, the term of this patent is extended or adjusted under 35 U.S.C. 154(b) by 191 days.

(21) Appl. No.: 11/224,489

(22) Filed: Sep. 12, 2005

(65) Prior Publication Data

US 2006/0058819 A1     Mar. 16, 2006

Related U.S. Application Data

(60) Provisional application No. 60/608,816, filed on Sep. 10, 2004.

(51) Int. Cl.
*H04R 25/00*     (2006.01)

(52) U.S. Cl. ...................................... 600/25

(58) Field of Classification Search ................ 600/25; 623/10, 11; 607/55–57; 181/126, 129; 606/60–61, 130
See application file for complete search history.

(56) References Cited

U.S. PATENT DOCUMENTS

| | | | |
|---|---|---|---|
| 4,655,776 A | 4/1987 | Lesinski | 623/10 |
| 4,729,366 A | 3/1988 | Schaeffer | 128/1.6 |
| 4,850,962 A | 7/1989 | Schaeffer | 600/25 |
| 4,922,333 A | 5/1990 | Nutting et al. | 358/78 |
| 4,957,478 A | 9/1990 | Maniglia | 600/25 |
| 4,969,900 A | 11/1990 | Fleischer | 623/10 |
| 5,015,224 A | 5/1991 | Maniglia | 600/25 |
| 5,024,224 A | 6/1991 | Engebretson | 128/420.6 |
| 5,085,628 A | 2/1992 | Engebretson et al. | 600/25 |
| 5,163,957 A | 11/1992 | Sade et al. | 623/10 |
| 5,217,011 A | 6/1993 | Bisch | 128/420.6 |
| 5,498,226 A | 3/1996 | Lenkauskas | 600/25 |
| 5,531,787 A | 7/1996 | Lesinski et al. | 623/10 |
| 5,549,658 A | 8/1996 | Shannon et al. | 607/57 |
| 5,558,618 A | 9/1996 | Maniglia | 600/25 |

(Continued)

FOREIGN PATENT DOCUMENTS

WO        WO 9829058 A    *  7/1998

OTHER PUBLICATIONS

US 5,282,011, 02/1994, Bisch et al. (withdrawn).

*Primary Examiner*—Charles A. Marmor, II
*Assistant Examiner*—Christine D. Hopkins
(74) *Attorney, Agent, or Firm*—Marsh Fischmann & Breyfogle LLP

(57) ABSTRACT

An improved apparatus and method is provided for supportably mounting an implantable hearing aid device to a patient's skull. The apparatus includes a support member adapted for supporting a hearing aid device and a plurality of mounting legs extending laterally from the support member in differing directions. The apparatus further includes a mechanism for use in conforming the mounting legs to the topology of a patient's skull. In one arrangement, the mechanism includes a plurality of guide legs having a reduced yield strength in comparison to the mounting legs. The reduced yield strength guide legs may be more readily conformed to the topology of the patient's skull to provide a mounting leg profile. Accordingly, the mounting legs may be deformed to match the profile of the guide legs such that a conformal fit between the apparatus and the patient's skull may be achieved.

29 Claims, 9 Drawing Sheets

U.S. PATENT DOCUMENTS

| | | | |
|---|---|---|---|
| 5,702,342 A | 12/1997 | Metzler et al. | 600/25 |
| 5,749,912 A | 5/1998 | Zhang et al. | 607/57 |
| 5,788,711 A | 8/1998 | Lehner et al. | 606/130 |
| 5,836,863 A | 11/1998 | Bushek et al. | 600/25 |
| 5,906,635 A | 5/1999 | Maniglia | 607/57 |
| 5,984,859 A | 11/1999 | Lesinski | 600/25 |
| 5,999,632 A | 12/1999 | Leysieffer et al. | 381/328 |
| 6,001,129 A | 12/1999 | Bushek et al. | 623/10 |
| 6,010,532 A | 1/2000 | Kroll et al. | 623/10 |
| 6,293,903 B1 * | 9/2001 | Kasic et al. | 600/25 |
| 6,325,755 B1 | 12/2001 | Bushek et al. | 340/14.69 |
| 6,398,717 B1 | 6/2002 | Leysieffer et al. | 600/25 |
| 6,491,622 B1 | 12/2002 | Kasic, II et al. | 600/25 |
| 6,517,476 B1 | 2/2003 | Bedoya et al. | 600/25 |
| 6,547,715 B1 | 4/2003 | Muller et al. | 600/25 |

* cited by examiner

ADJUSTABLE BONE BRACKET

CROSS REFERENCE TO RELATED APPLICATIONS

This application claims the benefit of the filing date of U.S. Provisional Application No. 60/608,816 entitled: "Adjustable Bone Bracket" having a filing date of Sep. 10, 2004, the contents of which are incorporated herein by reference.

FIELD OF THE INVENTION

The present specification relates to an apparatus and method for supportably mounting an implantable hearing aid device to a patient's skull, and more particularly, to a mounting apparatus that provides ease of installation advantages.

BACKGROUND OF THE INVENTION

In the class of hearing aid systems generally referred to as implantable hearing instruments, some or all of various hearing augmentation componentry is positioned subcutaneously on or within a patient's skull. By way of primary example, such devices include those that utilize electromechanical or piezoelectric transducers for stimulation of the ossicular chain (see, e.g., U.S. Pat. No. 5,702,342), and those which utilize excitor coils to electromagnetically stimulate magnets affixed above to a bone in the middle ear (see, e.g., U.S. Pat. No. 5,897,486). Additional implantable approaches employ piezoelectric transducers to stimulate the ossicular chain.

In most instances, hearing aid devices of the above-noted nature entail supportably mounting at least a portion of a middle ear actuator to a patient's skull, wherein the supported portion is positioned in an opening surgically defined in the skull. Most typically, the supported portion is at least partially located within the mastoid process and requires stable and reliable placement. However, desirable locations for skull interconnection may be limited and can vary significantly from patient-to-patient, thereby adding to implant procedure complexity. In this regard, the required time associated with mounting during implant procedures is of growing concern given the high costs associated with surgical facility usage and the baseline objective of making implantable hearing aid devices an affordable option for the hearing impaired.

SUMMARY OF THE INVENTION

In view of the foregoing, one objective is to provide an apparatus and method for implantable hearing aid device mounting that provides positioning-flexibility and enhanced stability.

A further objective is to provide an apparatus and method for implantable hearing aid device mounting that can be implemented with reduced installation time and attendant cost relative to many current mounting devices/methods.

The above objectives and additional advantages may be realized by the apparatus and method disclosed herein. The apparatus comprises a support member adapted to support an implantable hearing aid device, or other implantable device, relative to an attachment surface and/or aperture of a patient bone. In one arrangement, the support member may be sized for placement through an aperture in the bone. The apparatus further includes at least one mounting leg, and more generally a plurality of mounting legs interconnected to and extending laterally away from the support member in a corresponding plurality of differing directions. Each of the plurality of mounting legs includes at least one mounting aperture for selectively receiving a bone attachment device therethrough. Furthermore, the apparatus includes a conformance mechanism for conforming each mounting leg to the attachment surface.

Accordingly, to a first aspect, the apparatus includes a guide leg interconnected to and extending laterally away from the support member for use in conforming the mounting leg to an attachment surface (e.g., a bone of a patient). The guide leg has a yield strength along its length that is less than the minimum yield strength along the length of the mounting leg. In this regard, the guide leg is more readily conformable to an attachment surface when the support member is placed in a desired position relative to the attachment surface. Utilization of the reduced yield strength guide leg allows for conforming the guide leg relative to a patient's skull (e.g., by hand) to define a desired contour or profile for the mounting leg. That is, upon conforming the guide leg to an attachment surface, the support member may be removed from the desired position relative to the attachment surface and the mounting leg may be deformed to match a profile defined by a corresponding guide leg.

As used herein, the term "yield strength" refers to plastic deformation (e.g., where the deformation remains after the stress is removed) of a body caused by an applied stress. This is in contrast to elastically deformation where a body returns to its original shape after an applied stress is removed. For any material, a yield strength (also known as an elastic limit) is the separation point between elastic and plastic deformation characteristics. That is, an applied stress beneath the elastic limit results in elastic deformation, whereas an applied stress above the elastic limit results in plastic deformation (or breakage for brittle materials).

As will be appreciated, the elastic limit or total yield strength of any member is generally dependant on one or more physical and material factors. These factors include the moment of inertia about an axis which a stress is applied (i.e. which is dependant upon the physical dimensions of the member) as well as the modulus of elasticity of the material forming the member. Accordingly, the, material, size and/or cross-sectional shape of the guide leg may be selected to provide a desired minimum yield strength along its length that is less than the minimum yield strength along the length of the mounting leg. Of note, the guide leg may have a constant yield strength along its length, or, the yield strength may vary along its length.

In one arrangement, the support member may include a plurality of mounting leg. To facilitate conformance of the plurality of mounting legs the support member may also include a corresponding plurality of the guide legs, wherein each of the guide legs has a yield strength along its length that is less than the minimum yield strength along the length of a corresponding one of the mounting legs. Likewise, the mounting legs and guide legs may radiate from the support member in corresponding different directions. In one arrangement, each guide leg may be disposed in a substantially adjacent position relative to a corresponding mounting leg. Irrespective of their exact location, it is desirable that the guide legs are positioned such that a profile defined by each such guide leg is reflective of the topology of the attachment surface onto which a corresponding mounting leg will be attached. Typically, the length of the guide legs will be equal to or greater than the length of the mounting legs such that an accurate profile of the attachment surface topology may be provided for the entire length of the mounting legs. However, this is not required.

In order to have minimum yield strength along its length that is less than the minimum yield strength of the mounting leg, one or more physical characteristics of the guide leg may be selectively adjusted. For instance, the cross-sectional area and/or cross-sectional shape of the guide leg may be adjusted to provide a desired stiffness. Typically, the guide leg will have an cross-sectional size that is less than the cross-sectional size of a corresponding portion of a corresponding mounting leg (i.e., a mounting leg for which the guide leg provides a contour/profile). Alternatively, the guide leg may have one or more sections having a reduced cross-sectional area to facilitate bending of those sections.

The guide leg may be integrally formed with the apparatus. In this regard, the guide leg may be formed of the same material(s) as the mounting leg. However, the guide leg may also be made of a dissimilar material having greater ductility/malleability than the material forming the mounting leg. For instance, the mounting leg may in some instances be made of a titanium material, whereas the guide leg may be made of a "softer" material(s). As will be appreciated, this may require fusing dissimilar materials. What is important is that the guide leg will plastically deform in view of an applied stress that is less than an applied stress required to plastically deform the mounting leg.

In another arrangement, the guide leg(s) may be part of a removable guide assembly that may be attached to, for example, the support member and/or the mounting leg(s). As will be appreciated, utilization of a removable guide assembly may facilitate the use of dissimilar materials and may allow for use of materials that are not necessarily biocompatible for extended periods. In the latter regard, almost any material may be utilized. Further, such a removable guide assembly may be utilized with existing support structures so long as the guide assembly is connectable to that structure during positioning.

The mounting leg may also include one or more physical characteristics that facilitate its conformance to a profile defined by a corresponding guide leg. For instance, the mounting leg may include one or more flexible portions disposed along its length having a yield strength or bending moment that is less than a yield strength or bending moment of remaining portions of the mounting leg. In this regard, deflection of the mounting leg in view of an applied stress may be isolated to one or more such flexible portions.

According to a second aspect, the mounting leg(s) of the apparatus are formed to facilitate conformance with an attachment surface. Specifically, each mounting leg includes a flexible portion disposed between the mounting aperture and the support member. This flexible portion has a bending moment that is less than the bending moment of at least one adjacent portion of the mounting leg. In this regard, the flexible portion facilitates conformance of the mounting leg to the attachment surface. For instance, such flexible portions may include, without limitation, a hinge member, an area having a reduced cross-sectional area in relation to a cross-sectional area of an adjacent portion of the mounting leg, an area having a reduced moment of inertia about a given axis in relation to a moment of inertia about the same axis of adjacent portions of the mounting leg and/or an area having an increased ductility in relation to the ductility of adjacent portions of the mounting leg.

In the arrangement where the flexible portion includes a hinge member, such a hinge member may further include a stop for limiting movement of the hinge member after the mounting leg is conformed to the attachment surface. Such a stop may include an attachment device for attaching each flexible portion of the mounting leg relative to the attachment surface. Alternatively, where the flexible portion is a hinge member, the stop may be any mechanism that eliminates relative movement of mating members of the hinge once in a desired position. For instance, the hinge may be deformable after the mounting leg is disposed in a desired position. In this arrangement, the hinge may be crimped or otherwise compressed to eliminate movement between hingedly connected portions of the mounting leg and/or support member. Accordingly, to enhance such functionality, one or more interfacing surfaces of the hinge may be serrated such that crimping/compression interlocks serrations on mating surfaces. Alternatively, an oversized hinge pin may be utilized (e.g., tapered) such that once the mounting leg is disposed in the desired position, the oversized hinge pin may be forced through apertures within the hinge and thereby prevent further rotative movement of the hinge. Such an oversized hinge pin may also be serrated.

In an arrangement where the flexible portion of the mounting leg is one or more areas along the length of the mounting leg having a reduced cross-sectional area (e.g., having a reduced bending moment), the shape of the reduced cross-sectional area may be different than the cross-sectional shape of other portions of the mounting leg. Alternatively, the flexible portions may be formed of a material having an increased ductility (e.g., a softer material) in comparison to the materials forming the adjacent portions of the mounting leg. Further, such different material sections (e.g., more ductile) may incorporated into one or more areas along the length of the mounting leg. Again, what is important is that the application of an applied stress to the mounting leg (e.g., at its distal end) will result in the flexible portion deforming prior to the remainder of the leg deforming.

In a further arrangement of the present aspect an adjuster may be incorporated with each mounting leg. Such an adjuster may allow for selectively adjustable movement of a portion of the mounting leg and/or the support member after the mounting leg has been attached to the attachment surface. For instance, such an adjuster may apply a force between the patient's skull and the mounting leg to lift a portion of the mounting leg between an attachment device (e.g., screw) and the support member. As will be appreciated, by lifting a portion of the mounting leg between its attachment point and the support member, a portion of the support member may be directed relative to a patient's skull (e.g., directed towards a auditory component). This may facilitate interconnecting hearing aid componentry to a patient's auditory system (e.g., an ossicle, oval window, tympanic membrane and/or cochlea). Examples of adjusters that may be utilized include, without limitation, jack screws disposed through a portion of each leg and/or wedges that may be inserted beneath each leg. In an arrangement where a jack screw is utilized, a support plate may be disposed beneath the jack screw to provide a solid support surface.

A method for conforming a mounting apparatus to an attachment surface of a bone is also disclosed. The method is directed to use of a mounting apparatus that includes a support member and a plurality of mounting legs interconnected to and extending laterally from a support member in different directions. Further, the apparatus includes a plurality of guide legs interconnected to and extending laterally away from the support member. In particular, the method includes the steps of positioning the support member of the mounting apparatus relative to a surface of a patient bone (e.g., into an opening defined in a patient's skull), and conforming at least one guide leg relative to the attachment surface. Once the at least one guide leg is conformed (e.g., to define an attachment surface topology profile), the mounting apparatus may be removed from the attachment surface and a mounting leg corresponding to the conformed guide leg may be deformed/bent to match the profile defined by the guide leg. As will be appreciated, the plurality (e.g., all) of the guide legs may be conformed while the support member is positioned relative to the attachment surface. Likewise, all of the mounting legs may be deformed to match corresponding guide legs upon removal from the attachment surface. As will be appreciated, this may reduce the number of iterations required to fit the mounting apparatus to an attachment surface.

Once all the mounting legs are deformed, the guide legs may, optionally, be removed from the mounting legs. This may entail cutting or breaking the guide legs from the support member and/or removing a removable guide from the support member. In any case, the support member may be repositioned relative to the attachment surface and the deformed mounting legs may be interconnected to the attachment surface.

Once the mounting legs are secured to the attachment surface, an adjuster may be utilized to adjust a position of one or more mounting legs to direct support member to a desired orientation.

Numerous additional aspects and variances will be apparent to those skilled in the art upon consideration of the further description that follows. Furthermore, it will be noted that additional combinations of the above-identified aspects may be utilized. For instance, such variations may include a support member having mounting legs, flexible portions, adjusters and/or guide legs in any appropriate combination.

DETAILED DESCRIPTION

Set forth herein is a mounting apparatus and method for supportably mounting an implantable device to an attachment surface of a bone of a patient. As discussed herein, the mounting apparatus is utilized for mounting an implantable hearing device relative to patient's skull, however, it will be appreciated that certain aspects of the apparatus are not limited to implantable hearing devices and/or skull attachment and may be utilized to attach other devices to other bones. As presented herein, the mounting apparatus includes a support member adapted for supporting an implantable device and a plurality of mounting legs extending laterally from the support member in different directions. Furthermore, the mounting apparatus utilizes one or more conformance mechanisms to facilitates the deformation of the mounting legs relative to an attachment surface to enhance conformance of the mounting apparatus to the surface as well as provide improved position flexibility while further improving overall ease of installation.

Figure 1:
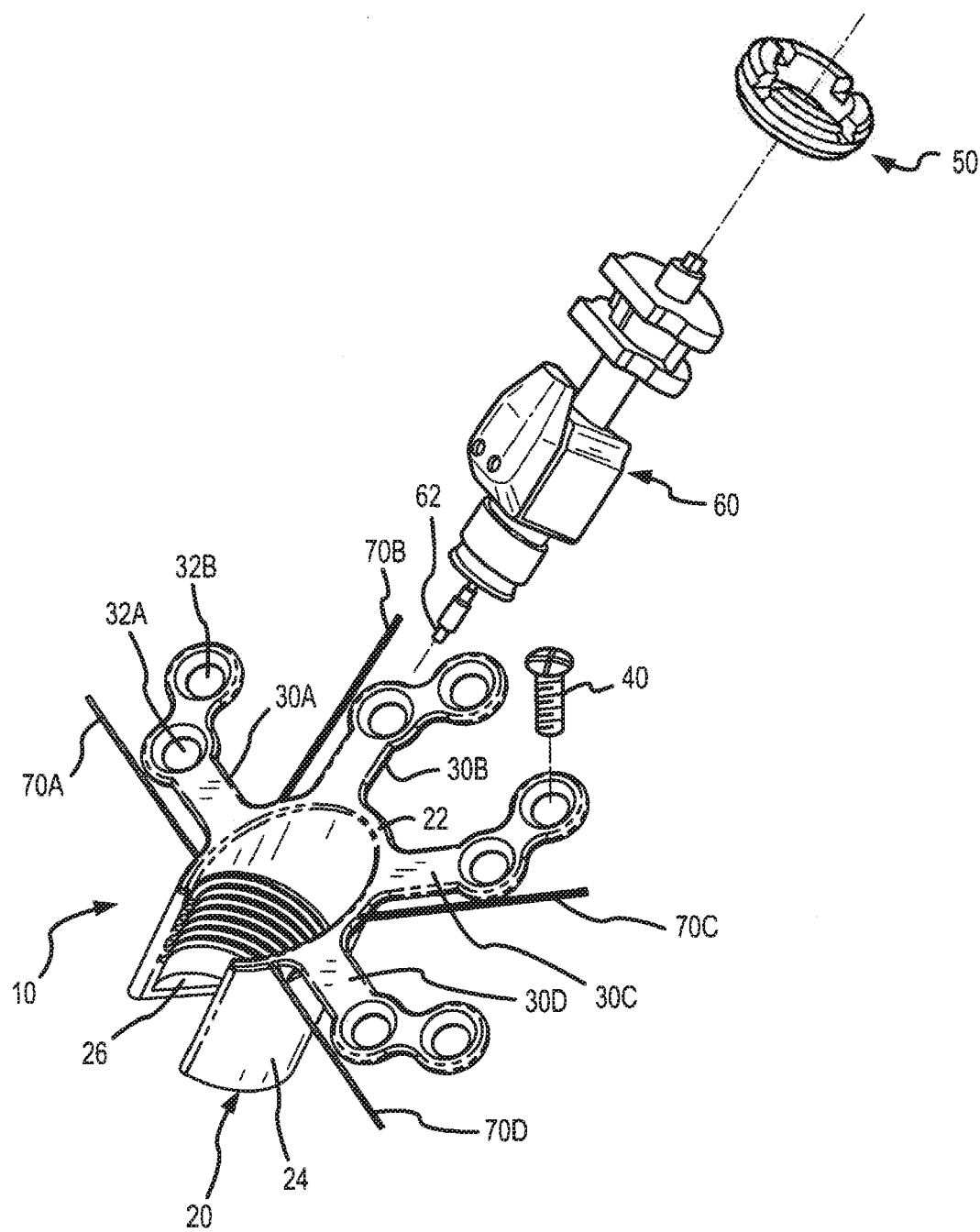
FIG. 1 illustrates a first embodiment of a mounting apparatus, together with an exemplary hearing aid device.

FIG. 1 shows a first embodiment of the mounting apparatus 10. In this embodiment, the mounting apparatus includes four mounting legs 30A-30D that radially extend in different directions from a first end 22 of a support member 20. As shown, each of the mounting legs 30A-D include a base that adjoins the support member 20 and at least one, and more preferably a plurality of apertures 32A-32B. The apertures 32A-B are each provided to selectively receive an attachment device 40 (e.g., a screw) therethrough for attachment to, in the present embodiment, a patient's skull. For such purposes, each of the apertures 32A-B may be beveled on a topside to facilitate secure interconnection with a complimentary shaped surface of attachment devices 40, while also reducing the overall profile of the apparatus upon interconnection. Though shown with two apertures 32A-B, it will be appreciated that additional apertures may be included.

As shown in FIG. 1, the support member 20 is defined by a cylindrical barrel 24 through which an implantable hearing aid device may be selectively and supportably positioned. Particularly, an exemplary hearing aid device 60 (e.g., an electromechanical transducer) is shown for use with the mounting apparatus 10. As illustrated, the barrel of the support member 20 may be provided with an end plate 26 on which at least a portion of the implantable hearing aid device 60 may be supportably received. Further, a portion of an inside surface of the barrel 24 may be threaded to receive a locking ring 50 and thereby supportably capture a portion of the implantable hearing aid device 60 between the locking ring 50 and end plate 26. In conjunction with the mounting apparatus 10 being implanted within a patient's skull and the hearing aid device 60 being secured therein, an actuator end 62 of the device 60 may be interconnected to a middle ear component (e.g., an ossicle bone) to provide mechanical stimulation thereof. A further description of such a mounting apparatus 10 and hearing aid device is provided in U.S. Pat. No. 6,293,903, entitled "Apparatus and Method for Mounting Implantable Hearing Aid Device", issued Sep. 25, 2001, the contents of which are incorporated herein by reference.

Figure 2A:
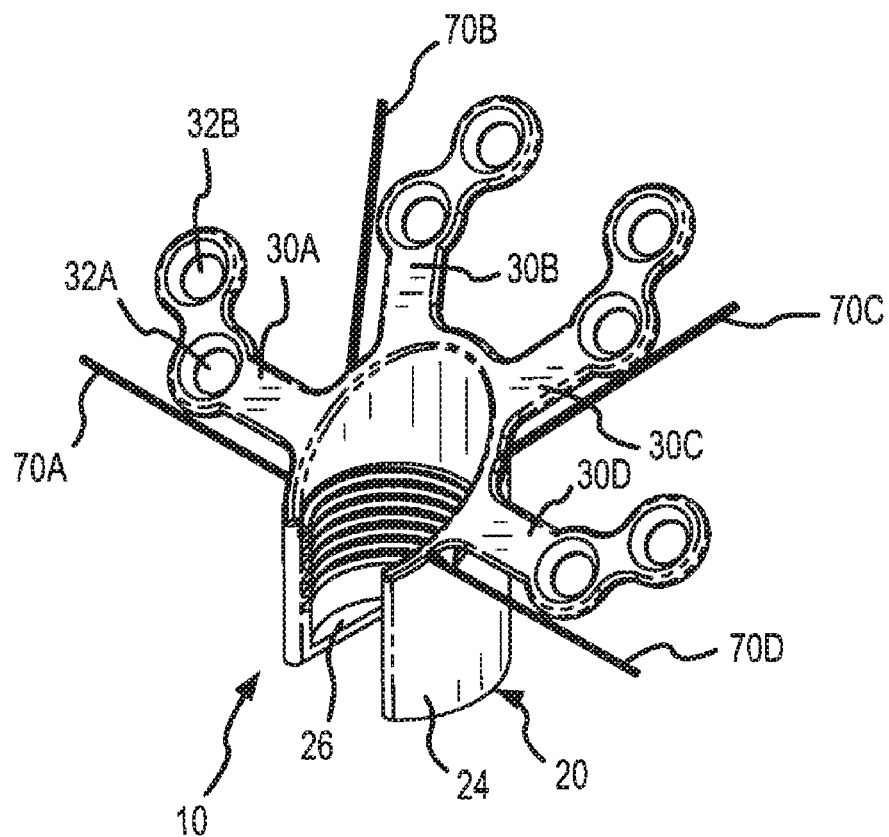
FIG. 2a shows a perspective view of the first embodiment of the mounting apparatus.
Figure 2B:
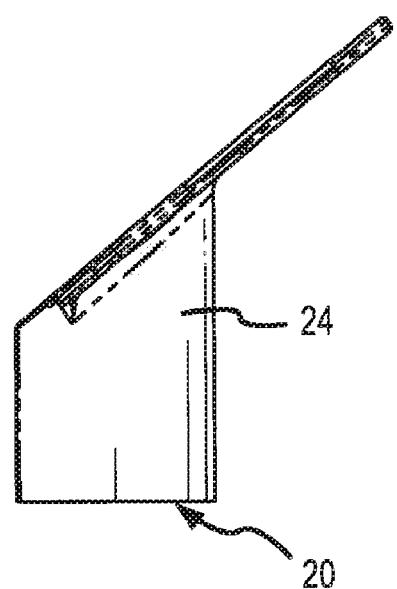
FIG. 2b shows a side view of the first embodiment of the mounting apparatus.

As shown in FIGS. 2A and 2B, the mounting legs 30A-D each adjoin the top end of the support member 20 in a substantially common plane in order to provide a low profile fit against the patient's skull. As shown, the support member 20 is disposed at an acute angle relative to the common plane. Such angular offset may facilitate the positioning of a hearing aid device (e.g., a middle ear actuator) by the mounting apparatus 10 in a desired location within a patient's skull. However, such an angular offset is not required. Further, the mounting legs 30A-D may be provided to be bendable up/down within a predetermined angular range relative to the support member 20. The bendable mounting legs 30A-D facilitate conformal interconnection of the mounting apparatus 10 to the skull, thereby yielding a low profile mounting apparatus that may provide for improved patient comfort.

Bending the mounting legs 30A-D to conform to the patient's skull may, in some instances, require that the mounting apparatus 10 be repeatedly inserted into an aperture defined within a patient's skull such that the position of each mounting leg 30A-D may be identified relative to the topology of the skull. Accordingly, the mounting apparatus 10 may be inserted and removed such that each mounting leg 30A-D may be adjusted to provide a more conformal fit. As will be appreciated, this may result in increased surgical time as well as poor conformance of the mounting legs 30A-D to the topology of the patient's skull. Accordingly, the present mounting apparatus includes one or more conformance mechanisms that allows for more readily conforming the mounting legs 30A-D to an attachment surface of the skull of a patient.

As shown in FIGS. 1 and 2, a first embodiment of the conformance mechanism for conforming the mounting legs 30A-D to an attachment surface includes a plurality of guide legs 70A-D or "whiskers." These guide legs 70A-D correspond to the number of mounting legs 30A-D and are each typically disposed substantially adjacent to a corresponding mounting leg 30A-D. Generally, the guide legs 70A-D have a reduced yield strength (e.g., stiffness) in comparison to their corresponding mounting legs 30A-D. As used herein, the term "yield strength" refers to plastic deformation (e.g., where the deformation remains after the stress is removed) of the guide leg caused by an applied stress. This yield strength may be constant along the length of the guide leg or may vary, for example, with a varying cross-sectional size of the guide leg. In any case, it is preferable that a guide leg deforms more readily than its corresponding mounting leg 30A-D. In this regard, the minimum yield strength along the length of a guide leg 70 will typically be less than a minimum yield strength along the length of a corresponding mounting leg 30.

Generally, the reduced yield strength will allow the guide legs 70A-D to be readily conformed to the topology of the patient's skull while the mounting apparatus 10 is disposed in an aperture of the skull. Accordingly, once the mounting apparatus 10 is removed from the skull, each mounting legs 30A-D may be deformed to match the contour defined by the corresponding guide leg 70A-D. As will be appreciated, this may reduce the number of iterations required to conformally fit the mounting legs 30A-D to the skull of the patient. Likewise, this may reduce surgical time and/or patient discomfort while providing an improved fit.

As noted, the yield strength of the guide legs 70A-D is reduced in comparison to the yield strength of the mounting legs 30A-D. This may be accomplished in a number of different ways. As shown, the guide legs 70A-D have a substantially reduced cross section in relation to the cross section of the mounting legs 30A-D. Accordingly, the guide legs 70A-D have a significantly reduced bending moment. In addition to having a reduced cross section, the guide legs 70A-D may also be formed of a separate material that may have, for example, a greater malleability than the material of the mounting legs 30A-D. However, it will be appreciated that the guide legs 70A-D and mounting legs 30A-D may also be formed of the same material such that the mounting apparatus 10 including the mounting legs 30A-D and guide legs 70A-D are an integrally formed unit.

Figure 3:
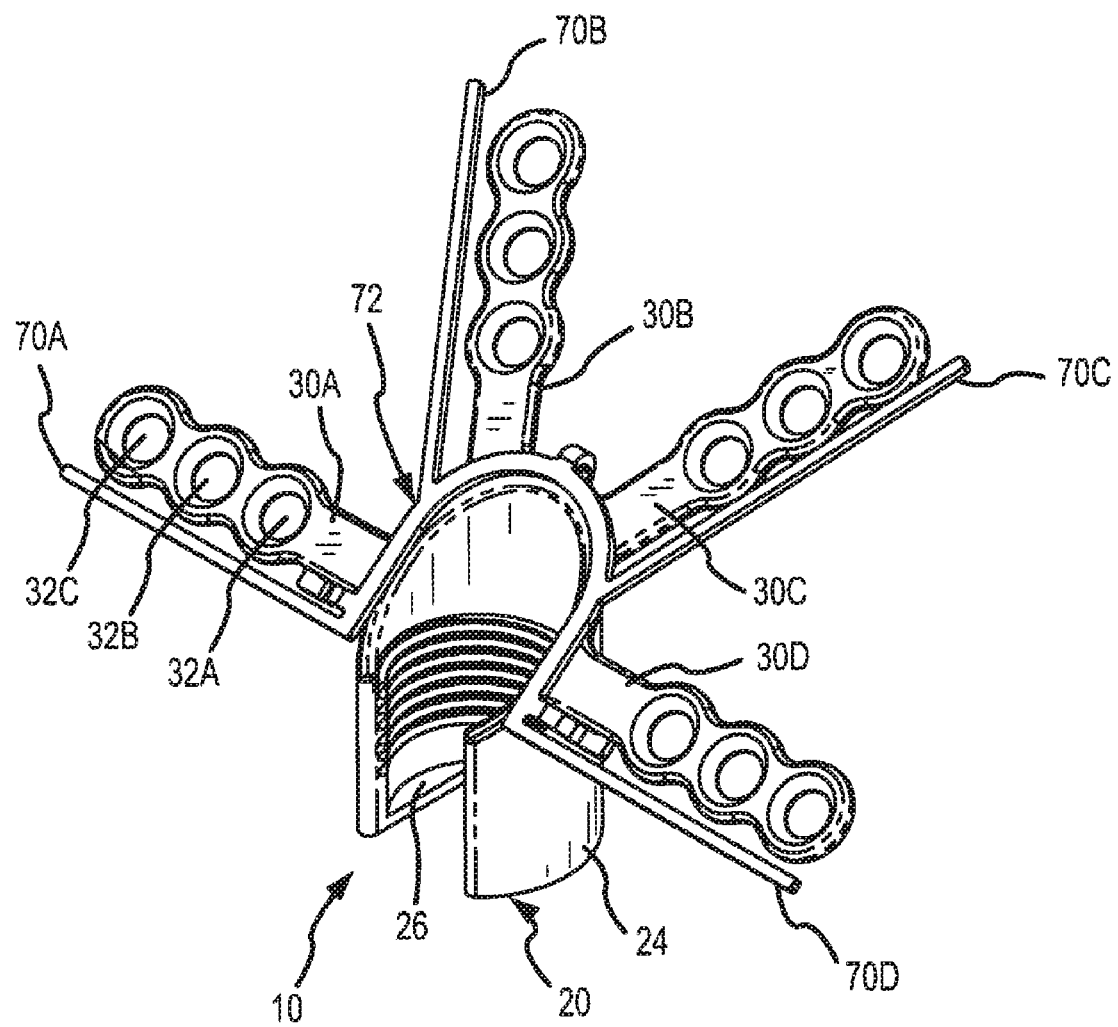
FIG. 3 illustrates a second embodiment of the mounting apparatus.
Figure 4:
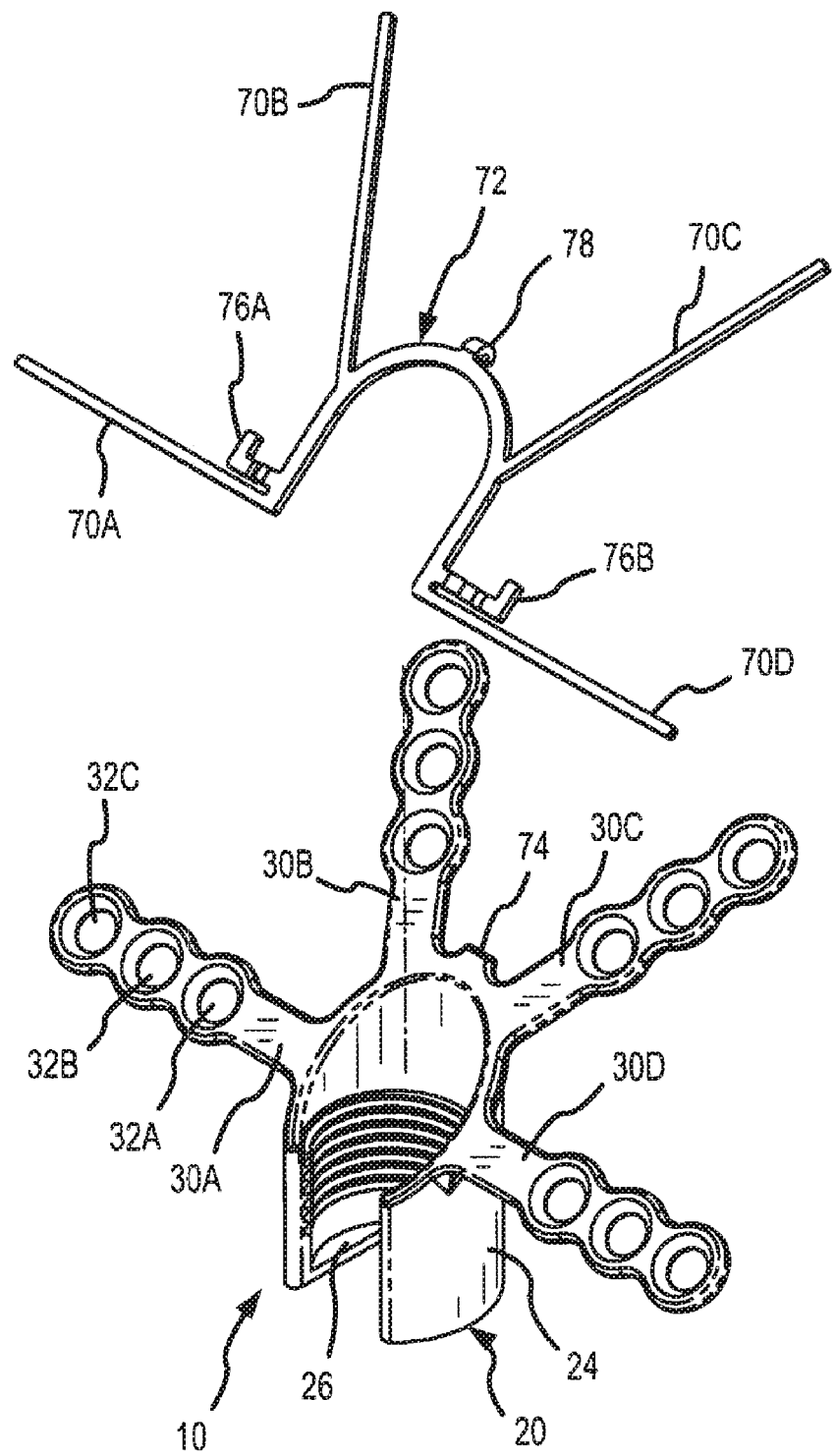
FIG. 4 shows an exploded view of the second embodiment of the mounting apparatus.

FIG. 3 shows a second embodiment of a mounting apparatus 10 that utilizes a plurality of guide legs 70A-D for use in conforming the mounting legs 30A-D to the skull of a patient. In the embodiment of FIG. 3, the plurality of guide legs 70A-D are formed on a removeable guide assembly 72 that may be selectively applied to the end of the mounting apparatus 10, as shown in FIG. 4.

The removeable guide assembly 72 includes three clips 76A, 76B and 78 for use in securing the guide 72 and its guide legs 70A-D relative to the end 22 of the mounting apparatus 10. In this regard, two opposing clips 76A, 76B are disposed beneath opposing mounting legs 30A and 30D while the body of the removeable guide assembly 72 is disposed against the end 22 of the mounting apparatus 20. Furthermore, a central clip 78 is utilized to maintain the center portion of the removeable guide assembly 72 relative to the end 22 of the support member 20. In this regard, the support member 20 further includes a nub 74 positioned to receive the central clip 78. However, it will be appreciated that the utilization of the central clip 78 and nub 74 is not required. For instance, each guide leg 70A-D may include its own clip for holding that guide leg 70A-D relative to a corresponding mounting leg 30A-D. Accordingly, it will be appreciated that such a removeable guide assembly 72 may be utilized with existing mounting apparatuses.

The use of a removeable guide assembly 72 facilitates the utilization of soft malleable materials for the guide legs 70A-D. That is, utilization of the removeable guide 72 allows for using a soft/malleable material (i.e., in comparison to the material utilized to form the mounting legs 30A-D) without the problems that may be associated with adjoining dissimilar materials in an integrally formed mounting apparatus incorporating "soft" guide legs. Of course, the cross-sectional size of the guide legs of a removable guide assembly 72 may also be reduced in comparison with the cross-sectional size of the mounting legs 30A-D.

Figure 5:
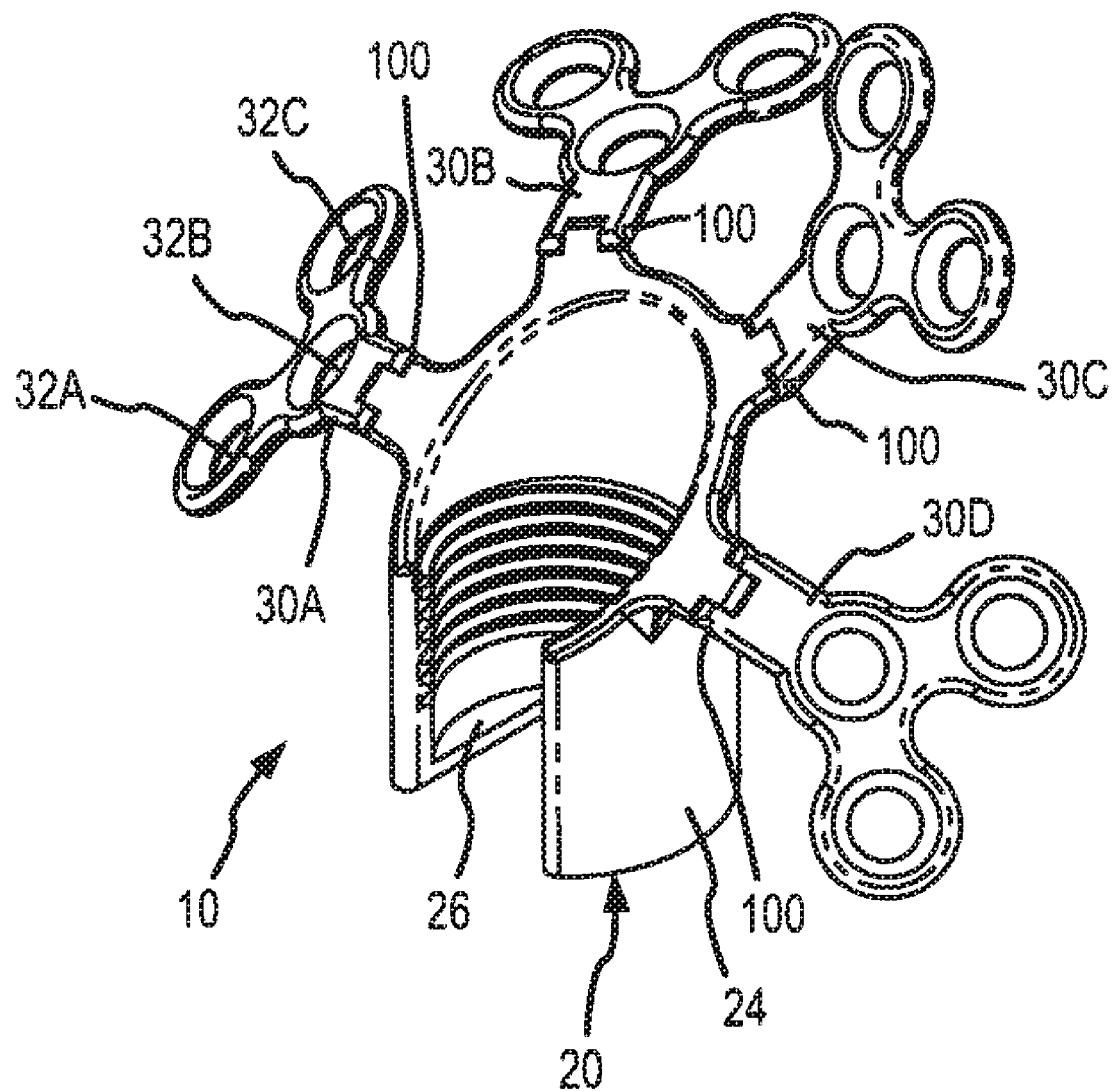
FIG. 5 illustrates a third embodiment of the mounting apparatus.

Another mechanism for conforming the mounting legs 30A-D relative to a patient's skull is shown in FIG. 5. In this embodiment, each mounting leg 30A-D incorporates a hinge member 100. As shown, the hinge member 100 is disposed between the base of each mounting leg 30A-D and distal end of each leg 30A-D. More particularly, the hinge member 100 is disposed between the base and at least one mounting aperture 32 in each leg. However, it will be appreciated that the hinge member 100 may be disposed more distally along each mounting leg 30A-D.

Figure 6A:
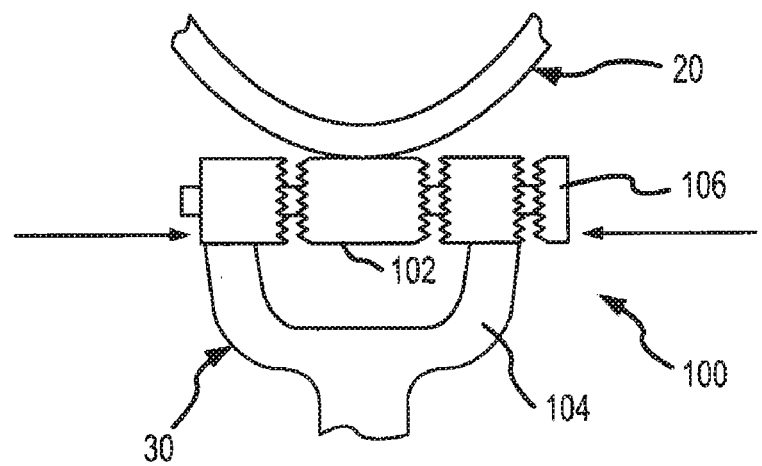
FIGS. 6a-6c illustrate optional components that may be utilized with the third embodiment.
Figure 6B:
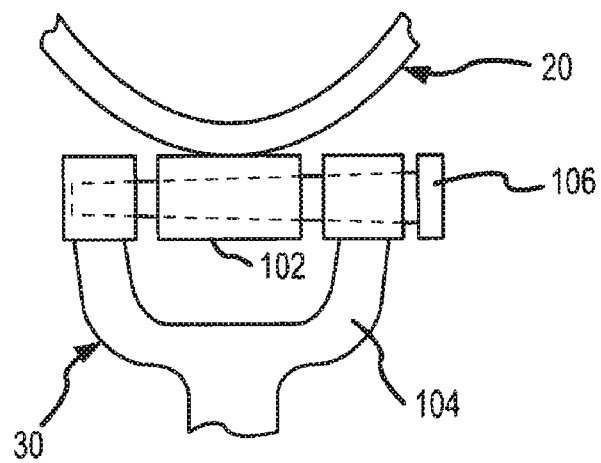
Figure 6C:
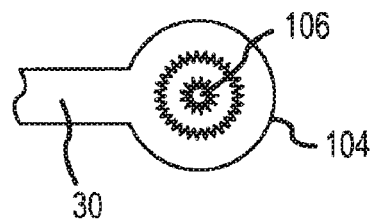

The hinge member 100 allows for each mounting leg 30A-D to conform relative to the patient's skull. In this regard, such hinge members 100 may eliminate the need to remove the mounting apparatus 10 for conforming purposes during implantation. However, to provide a secure fit for the support member 20, the flexibility of the hinge members 100 may have to be reduced and/or eliminated upon the mounting apparatus 10 being implanted. FIGS. 6A-C illustrate three stop mechanisms limiting and/or preventing movement of the hinge member 100 once the mounting legs 30A-D have been disposed in a desired position.

As shown in FIG. 6A, the hinge member 100 includes a knuckle 102 interconnected to the end of the support member 20, a clevis 104 attached to the guide leg 30 that includes opposing legs disposed on opposing sides of the knuckle 102, and a pin 106 extending through apertures in the first leg of the clevis 104, the knuckle 102, and the second leg of the clevis 104. Though discussed with the clevis 104 being disposed on the mounting leg 30 and the knuckle 102 being disposed on the support member 20, it will be appreciated that the members may be reversed. To limit the movement of the hinge member 100, the mating surfaces of the clevis 106 and knuckle 102 are matingly serrated. Furthermore, the inside surface of the head 108 of the pin 106 may also be serrated. Accordingly, by compressing the head 108 of the pin 106 and the outside edge of the second leg of the clevis 104 as shown in the arrows in FIG. 6A, the clevis 104 may be shaped such that serrations on the components mate and thereby prevent the hinge member 100 from moving.

FIG. 6B shows a second mechanism for limiting the movement of the hinge member 100. As shown, a tapered hinge pin 106 is utilized to interconnect the clevis 104 and the knuckle 102. In this regard, by pressing the tapered pin 106 through the mating components, a compressive force is formed between the pin 106 the clevis 104 and knuckle 102. Accordingly, movement of those components may be reduced and/or eliminated.

FIG. 6C shows a third mechanism that may be utilized alone and/or in combination with the above-noted mechanisms. As shown, FIG. 6C utilizes a serrated aperture through the clevis 104 and/or knuckle 102 as well as a serrated pin 106. In this regard, by placing each mounting leg 30A-D at a desired position on the skull, and providing a slight axial or compressive force to the mounting leg, serrations on the hinge pin 106 may meet with serrations on the inside surface of the aperture, thereby preventing further rotation of the mounting leg 30.

Figure 7A:
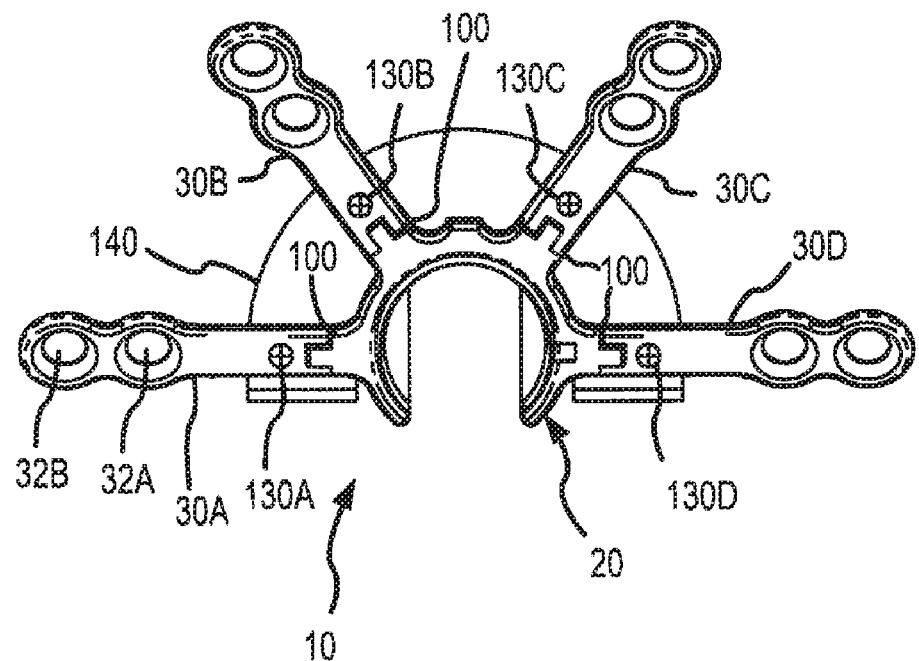
FIG. 7a illustrates a fourth embodiment of the mounting apparatus.

FIG. 7A shows a second embodiment of the mounting apparatus 10, which incorporates the hinge member 100. In addition to incorporating the hinge member 100, the mounting apparatus 10 further includes adjusters 130A-D for use in adjusting the position of the support member 20 after attachment to a patient's skull. As shown, the adjuster 130 comprises a jack screw that is disposed through each mounting leg 30A-D between the hinge member 100 and the aperture 32 of each mounting leg 30A-D. Optionally, the mounting apparatus 10 may further include a support plate 140 that may be positioned beneath the mounting legs 30A-D around the periphery of the support member 20. The support plate 140 may provide a solid surface against which the adjuster 130 may press to position the support member 20.

Figure 7B:
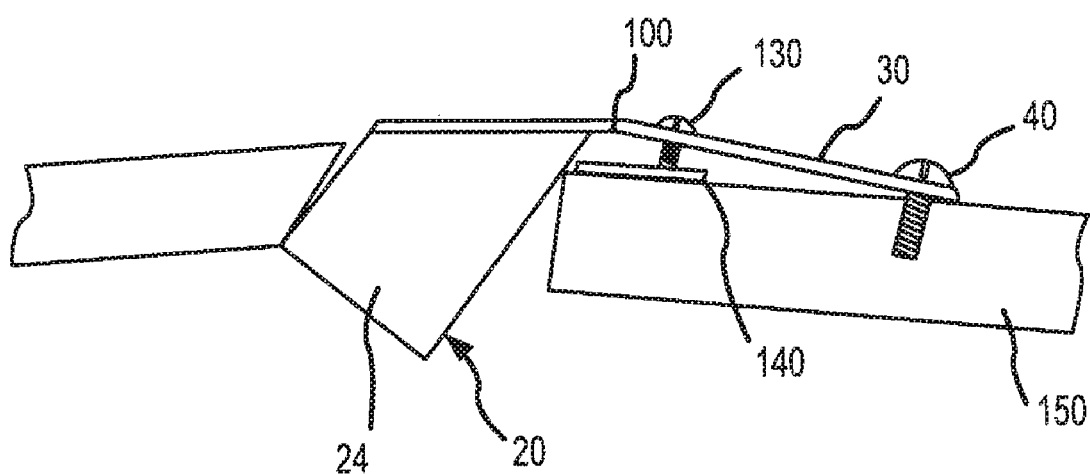
FIG. 7b shows the fourth embodiment upon interconnection to a patient's skull.

As shown in FIG. 7B, the mounting apparatus 10 is secured to a patient's skull 150. In this regard, the barrel 24 of the support member 20 is disposed through an aperture within the skull 150. Accordingly, an attachment device 40 may be disposed through one or more of the apertures 32A-B in each mounting leg 30A-D to affix each mounting leg 30A-D to the patient's skull 150.

While utilization of the hinge member 100 improves the conformance of the mounting apparatus 10 to the patient's skull 150, the barrel 24 of the mounting apparatus 10 may become misaligned with a middle ear component (e.g., an ossicle) during the attachment procedure. Accordingly, attachment of the hearing instrument 60 to the middle ear component may become problematic. In this regard, utilization of the adjusters 130A-D allows for post attachment alignment of the mounting apparatus 10 with, for example, a middle ear component.

As shown in FIG. 7B, the adjuster 130 may be adjusted (e.g., threaded in) such that a portion of the mounting leg 30 near the hinge member 100 is lifted off the surface of the patient's skull 150. In the case where the adjuster 130 comprises a jack screw, the tip of the jack screw may press against the support plate 140 (i.e., when utilized) and thereby lift a portion of the mounting leg 30 relative to the skull 150. Accordingly, by lifting a portion of the mounting leg 30 near the hinge member 100, the position of the barrel 24 of the mounting apparatus 10 may be adjusted. Accordingly, by adjusting all of the adjusters 130A-D, the barrel 24 may be aligned with a middle ear component to facilitate interconnection of a hearing instrument 60 thereto.

Though discussed in relation to the use of a jack screw, it will be appreciated that the adjuster 130 may be any component that is operable to move (e.g., lift) a portion of the mounting legs 30A-D in order to adjust the position of the barrel 24. For instance, wedges that may be inserted between the patient's skull 150 and/or the support plate 140 and each mounting leg 30 may also be utilized.

Figure 8:
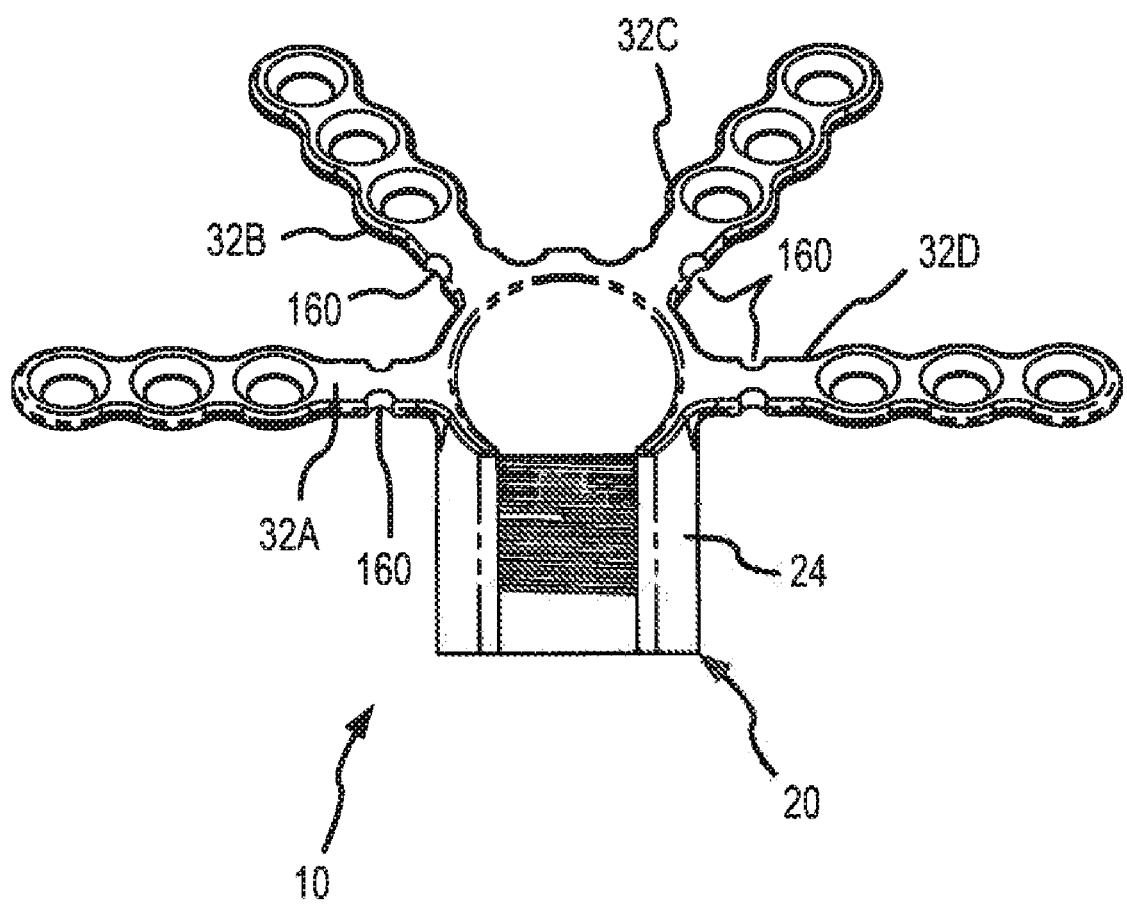
FIG. 8 illustrates a fifth embodiment of the mounting apparatus.

FIG. 8 shows a further embodiment of a mechanism for use in forming the mounting legs 30A-D relative to the patient's skull. In particular, each mounting leg 30A-D incorporates a flexible portion 160 disposed between the mounting apertures 32A-N and the support member 20. The flexible portion 160 has a bending moment that is less than the bending moment of an adjacent portion of the mounting legs 30A-D. As shown, the flexible portion 160 generally has a smaller cross-sectional area as compared to the cross-sectional area of adjacent portions of the mounting legs 30A-C. Of note, this reduced cross-sectional size may further incorporate a different cross-sectional shape (e.g., round vs. rectangular). What is important is that a flexible portion 160 of each mounting leg 30A-D will, in view of an applied stress, deflect/bend prior to another portion of the mounting leg 30A-D bending. As will be appreciated, utilization of the flexible portion 160 may also allow for in-place deflection of the mounting legs 30A-D when the mounting apparatus 10 is disposed within a patient's skull.

The flexible portion 160 may be formed of the same material as the remainder of each mounting leg 30. However, the flexible portion 160 may also be made of a dissimilar material (e.g., softer/less stiff material). In this latter regard, the flexible portion 120 may not require a reduced cross section relative to the remainder of the leg. Finally, it will be noted that variations may be made to the present embodiment. For instance, a number of flexible portions 160 may be disposed along the length of each mounting leg 30A-D to facilitate conformance along the entire length of the mounting leg.

Figure 9:
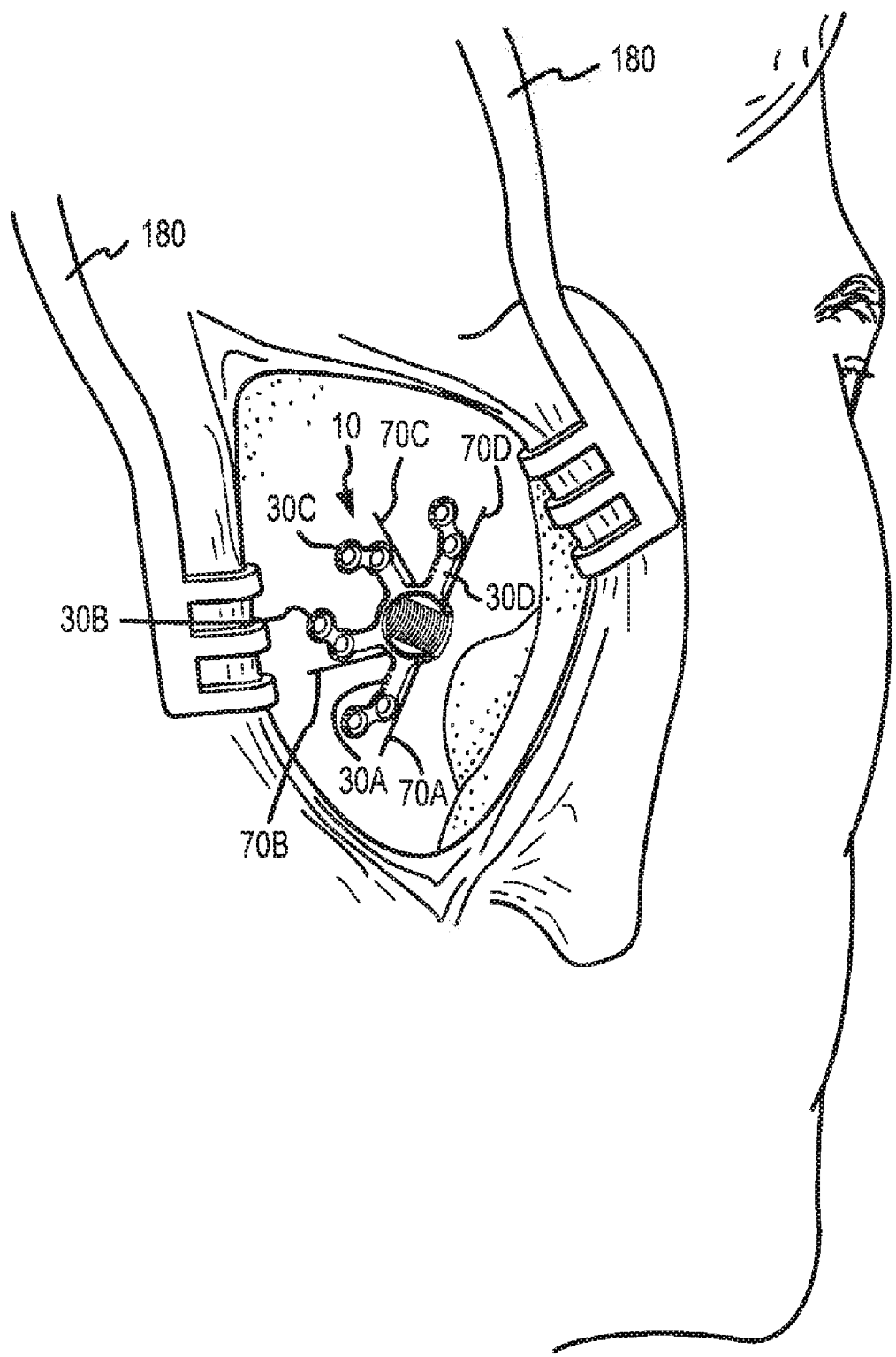
FIG. 9 illustrates the first embodiment upon interconnection to a patient's skull.

An exemplary use of the present invention will now be described with reference to FIG. 9. Initially, medical personnel access the mastoid process of a given patient via an incision made behind the patient's ear. Accessory devices 180 may be utilized for maintaining such assess during the implant procedure. Next, an access opening may be formed at a selected location thru the mastoid process (e.g., via drilling). Such access opening should be large enough to facilitate placement of a selected mounting apparatus 10 therethrough. In this regard, the particular mounting apparatus embodiment 10 utilized for a given patient may be selected from a plurality of different embodiments (e.g., the alternative embodiments shown above) as may be appropriate for a given patient. The selected mounting apparatus embodiment may then be positioned through the defined access opening. For purposes of this example, the mounting apparatus 10 of FIG. 1 utilizing guide legs 70 is described.

The above procedures may be completed with the access orientation of the mounting apparatus 10 selected so as to provide a straight-line access through the barrel portion 24 of the mounting apparatus 10 to the middle ear of the patient including, for example, the osticular chain and/or oval window. Following the desired positioning of the mounting apparatus 10, guide legs 70A-D may be bent into conformal skull engagement. Once the guide legs 70A-D are conformal with the skull, the mounting apparatus 10 may be removed from the access opening such that the mounting legs 30A-D may be deformed to match the contours/profiles defined by each guide leg 70A-D. The guide legs 70A-D may be removed from the mounting apparatus 10 if desired. In the case of the first embodiment wherein the guide legs 70A-D are integrally formed with the mounting apparatus 10, this may entail cutting or otherwise breaking the guide legs 70A-D from the support member 20. When utilizing the removeable guide leg apparatus, this may simply entail removing the removeable guide 72 from the mounting apparatus 10. In any case, once the guide legs 70A-D are removed, the mounting apparatus 10 may be reinserted within the access opening. Then the apparatus may be secured to the patient's skull via the insertion and interconnection of one or more attachment devices (e.g., screws) through one or more selected apertures 32A-N.

After placement of the apparatus 10, the implantable hearing aid device 60 may be supportably positioned into the cylindrical barrel 24 of the support member 20. By way of example, the implantable hearing aid device may comprise an electromechanical transducer having a probe tip adapted for selective contact positioning relative to a middle ear bone or oval window of a patient. Following the desired positioning of the implantable hearing aid device 60, connections to other components of the hearing aid system may be completed.

The foregoing description of the present invention has been presented for purposes of facilitating and understanding of the invention. Other embodiments, applications, and modifications will be apparent to those skilled in the art and are intended to be within the scope of the present invention as defined by the claims that follow.

What is claimed is:

1. An apparatus for supportably mounting an implantable device to a patient's bone, comprising:
    a support member adapted to support an implantable device relative to an attachment surface of a bone;
    a mounting leg interconnected to and extending laterally away from the support member, the mounting leg including at least one mounting aperture for selectively receiving a bone attachment device therethrough; and
    a guide leg interconnected to and extending laterally away from the support member, the guide leg having the guide leg has an average cross-sectional size that is less than an average cross-sectional size of the mounting leg, and wherein said guide leg has a minimum yield strength along it length that is less than a minimum yield strength along the length of the mounting leg.

2. The apparatus of claim 1, further comprising:
    a plurality of mounting legs; and
    a corresponding plurality of guide legs.

3. The apparatus of claim 2, wherein the plurality of mounting legs radiate from the support member in a corresponding plurality of different directions.

4. The apparatus of claim 3, wherein the plurality of guide legs radiate from the support member in the corresponding plurality of different directions.

5. The apparatus of claim 1, wherein the average cross-sectional size of the mounting leg is between 1.5 and 10 times the average cross-sectional size of the guide leg.

6. The apparatus of claim 1, wherein the guide leg is made of a first material and the mounting leg is made of a different second material.

7. The apparatus of claim 6, wherein the first material has a greater ductility than the second material.

8. The apparatus of claim 1, wherein the mounting leg includes a plurality of mounting apertures for selectively receiving a bone attachment device therethrough.

9. The apparatus of claim 1, wherein the mounting leg further includes:
    a flexible portion disposed between the mounting aperture and the support member, the flexible portion having a yield strength that is less than a yield strength of another portion of the mounting leg.

10. The apparatus of claim 9, wherein the flexible portion comprises at least one of:
    a hinge member;
    an area having a reduced cross-sectional area in relation to an average cross-sectional area of the mounting leg;
    an area having a reduced bending moment in relation to an average bending moment of the mounting leg;
    an area having an increased ductility in relation to the average ductility of the mounting leg.

11. The apparatus of claim 1, wherein the mounting leg further comprises a hinge member and the hinge member further includes a stop for selectively limiting movement of the hinge member.

12. The apparatus of claim 9, further comprising:
    an adjustor disposable between the mounting aperture and the flexible portion, the adjustor being operative to apply a force between the mounting leg and the attachment surface.

13. The apparatus of claim 12, wherein the adjustor comprises at least one of:
    a screw; and
    a wedge.

14. The apparatus of claim 1, wherein the mounting leg and the guide leg are integrally formed with the support member.

15. The apparatus of claim 1, wherein the guide leg is removeably attached to the support member.

16. An apparatus for supportably mounting an implantable hearing aid device to a patient's skull, comprising:
    a support member sized for placement through and adapted to support an implantable device within a patient's skull;
    a plurality of mounting legs interconnected to and extending laterally away from the support member, each of the plurality of mounting legs including:
        at least one mounting aperture for selectively receiving an attachment device therethrough; and
        a flexible portion disposed between the mounting aperture and the support member, the flexible portion having a bending moment that is less than a bending moment of an adjacent portion of the mounting leg; and
    a plurality of guide legs attached to and extending laterally away from the support member, each of the guide legs having an average stiffness that is less than an average stiffness of each of the mounting legs.

17. The apparatus of claim 16, wherein the flexible portion of each of the plurality of mounting legs includes at least one of:
    a hinge member;
    an area having a reduced cross-sectional area in relation to a cross-sectional area of the adjacent portion of the mounting leg;
    an area having a reduced moment of inertia in relation to a moment of inertia of the adjacent portion of the mounting leg
    an area having an increased ductility in relation to the ductility of the of the adjacent portion mounting leg.

18. The apparatus of claim 16, wherein the flexible portion comprises a hinge member and the hinge member further includes a stop for selectively limiting movement of the hinge member.

19. The apparatus of claim 16, wherein each of the plurality of mounting legs further comprise:
  an adjustor disposable between the mounting aperture and the flexible portion of the mounting leg, the adjustor being operative to apply a force between the mounting leg and an attachment surface.

20. The apparatus of claim 19, wherein the adjustor comprises at least one of:
  a screw; and
  a wedge.

21. The apparatus of claim 16, wherein the plurality of mounting legs and the plurality of guide legs are equal in number.

22. The apparatus of claim 21, wherein each of the plurality of guide legs have an average cross-sectional size that is less than an average cross-sectional size of the plurality of mounting legs.

23. The apparatus of claim 21, wherein at least one of the plurality of mounting legs and one of the plurality of guide legs are integrally formed with the support member.

24. The apparatus of claim 21, wherein the plurality of guide legs are removably attached to the support member.

25. An apparatus for supportably mounting an implantable device to a patient's bone, comprising:
  a support member adapted to support an implantable device relative to an attachment surface of a bone;
  a mounting leg interconnected to and extending laterally away from the support member, the mounting leg including at least one mounting aperture for selectively receiving a bone attachment device therethrough; and
  a guide leg interconnected to and extending laterally away from the support member, the guide leg having a minimum yield strength along it length that is less than a minimum yield strength along the length of the mounting leg, where in the guide leg is made of a first material and the mounting leg is made of a different second material.

26. The apparatus of claim 25, wherein the first material has a greater ductility than the second material.

27. An apparatus for supportably mounting an implantable hearing aid device to a patient's skull, comprising:
  a support member sized for placement through and adapted to support an implantable device within a patient's skull;
  a plurality of mounting legs interconnected to and extending laterally away from the support member, each of the plurality of mounting legs including:
  at least one mounting aperture for selectively receiving an attachment device therethrough; and
  a hinge member disposed between the mounting aperture and the support member, the hinge member allowing a distal end of the mounting leg to move relative to support member.

28. The apparatus of claim 27, wherein hinge member further includes a stop for selectively limiting movement of the hinge member.

29. The apparatus of claim 27, wherein each of the plurality of mounting legs further comprise:
  an adjustor disposable between the mounting aperture and the hinge member of the mounting leg, the adjustor being operative to apply a force between the mounting leg and an attachment surface.

* * * * *

UNITED STATES PATENT AND TRADEMARK OFFICE
CERTIFICATE OF CORRECTION

PATENT NO. : 7,326,171 B2  Page 1 of 1
APPLICATION NO. : 11/224489
DATED : February 5, 2008
INVENTOR(S) : Kasic et al.

It is certified that error appears in the above-identified patent and that said Letters Patent is hereby corrected as shown below:

Column 11, line 43, delete "it" and insert therefor --its--.
Column 12, line 63, after "portion" insert --of the--.
Column 14, line 1, delete "it" and insert therefor --its--.
Column 14, line 20, after the second occurrence of "to", insert --the--.
Column 14, line 22, after "wherein", insert --the--.

Signed and Sealed this

Third Day of March, 2009

JOHN DOLL
*Acting Director of the United States Patent and Trademark Office*